US00PP28502P3

(12) United States Plant Patent
Clark et al.

(10) Patent No.: US PP28,502 P3
(45) Date of Patent: Oct. 10, 2017

(54) BLUEBERRY PLANT NAMED 'NORMAN'

(50) Latin Name: ***Vaccinium corymbosum* L.**
Varietal Denomination:

(71) Applicants: THE BOARD OF TRUSTEES OF THE UNIVERSITY OF ARKANSAS, Little Rock, AR (US); THE UNITED STATES OF AMERICA, AS REPRESENTED BY THE SECRETARY OF AGRICULTURE, Washington, DC (US)

(72) Inventors: John Reuben Clark, Fayetteville, AR (US); James N. Moore, Arlington, TX (US); Arlen Draper, Payson, AZ (US)

(73) Assignees: The Board of Trustees of the University of Arkansas, Little Rock, AR (US); The United States of America, as Represented by the Secretary of Agriculture, Washington, DC (US)

( * ) Notice: Subject to any disclaimer, the term of this patent is extended or adjusted under 35 U.S.C. 154(b) by 55 days.

(21) Appl. No.: 14/757,151

(22) Filed: Nov. 25, 2015

(65) Prior Publication Data

US 2017/0150664 P1 May 25, 2017

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP10,035 P 9/1997 Moore et al.

OTHER PUBLICATIONS

Plant Breeders' Rights in Japan, Serial No. 29863, filed Jan. 13, 2015, 30 pp.*

* cited by examiner

*Primary Examiner* — June Hwu
(74) *Attorney, Agent, or Firm* — Andrus Intellectual Property Law, LLP

(57) ABSTRACT

Description and specifications of a new and distinct blueberry cultivar named 'Norman' which originated from seed produced by a hand-pollinated cross of USDA blueberry selection G-566 (non-patented, unreleased genotype)× 'Legacy' (non-patented, released genotype) is provided. This new blueberry cultivar can be distinguished by high fruit quality including excellent picking scar, color, firmness and flavor along with excellent plant health and vigor.

4 Drawing Sheets

Latin name: *Vaccinium corymbosum* L.

BACKGROUND

The new cultivar of blueberry called 'Norman' is described herein. The new cultivar originated from a hand-pollinated cross of USDA blueberry selection G-566× 'Legacy' made at Beltsville, Md. in 1985. Seedlings were grown and shipped to Fayetteville, Ark. in late winter of 1986 and planted in a field there in early spring of the same year. The seedlings fruited in the summer of 1989 and one seedling, designated 'A-272' herein described as 'Norman', was selected for major characteristics including high fruit quality including excellent picking scar, color, firmness and flavor along with excellent plant health and vigor.

SUMMARY OF THE INVENTION

The new and distinct cultivar of blueberry originated from a hand-pollinated cross of USDA blueberry selection G-566 (non-patented, unreleased genotype; female)×'Legacy' (non-patented, released genotype; male) made in 1985 at Beltsville, Md. The botanical designation of the new cultivar of blueberry is *Vacinnium corymbosum* L., as that is the primary species in its background, although there are other species in the pedigree including *V. darrowii* Camp and *V. angustifolium* Aiton.

Seedlings were grown and shipped to Fayetteville, Ark. (Northwest Arkansas) in late winter of 1986 and planted in a field there in early spring of the same year. The seedlings fruited in the summer of 1989 and one seedling, designated 'A-272' herein described as 'Norman', was selected for major characteristics including high fruit quality including excellent picking scar, color, firmness and flavor along with excellent plant health and vigor.

The original selected plant was removed from the seedling field and established at the same location (Fayetteville, Ark.). In 1997, hardwood cuttings were collected from this plant and an additional planting consisting of eight plants in a replicated trial were established near Clarksville, Ark. (West-central Arkansas). An additional eight plants were established in a replicated trial at Fayetteville, Ark. in 2001 that resulted from hardwood cuttings collected in 1999 from the original selected plant. Subsequently, the cultivar was propagated from hardwood cuttings from the Fayetteville, Ark. original selected plant at test plots in Aurora, Oreg., Oxnard, Calif. and Delano, Calif.

The new cultivar has been asexually multiplied since 2007 by the use of both hardwood cuttings. During all asexual multiplication, the characteristics of the original plant have been maintained and no aberrant phenotypes have appeared.

Test plantings over a wide geographic area have shown this new cultivar to be adapted and productive at both Arkansas locations as well as Aurora, Oreg. and Delano, Calif. locations. It did not show adaptation at Oxnard, Calif. as adequate chilling was not achieved for good plant performance.

The primary comparisons of 'Norman' have been with the cultivars 'Ozarkblue' (U.S. Plant Pat. No. 10,035) and 'Bluecrop' (not patented) in a planting near Clarksville, Ark.

BRIEF DESCRIPTION OF THE PHOTOGRAPHS

The accompanying photographs show typical specimens of the new cultivar in color as nearly true as it is reasonably possible to make in a color illustration of this character.

DETAILED DESCRIPTION OF THE NEW CULTIVAR 'NORMAN'

Figure 1:
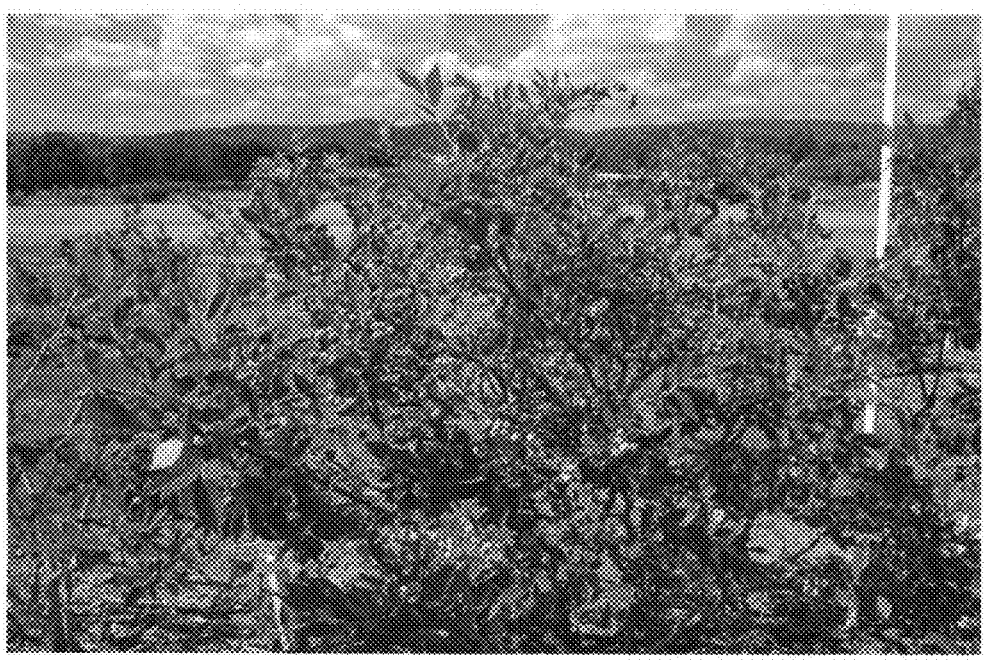
FIG. 1 is a photograph taken in mid-June of a mature 11 year old plant of 'Norman', near Clarksville, Ark.
Figure 2:
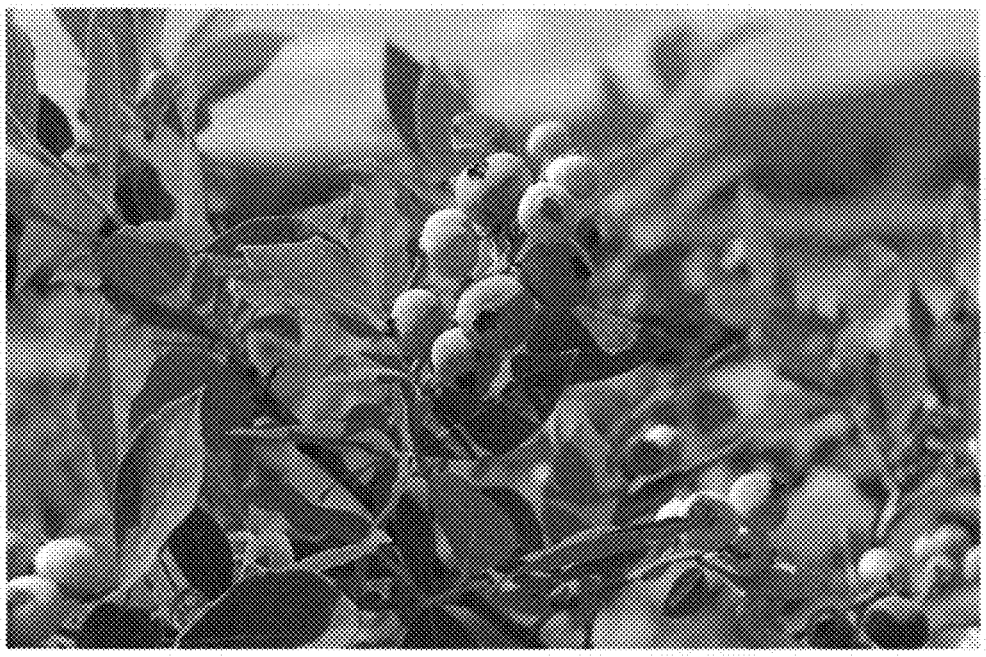
FIG. 2 is a photograph taken in late-June of fruits borne on a terminal branch near Clarksville, Ark. of 'Norman'.
Figure 3:
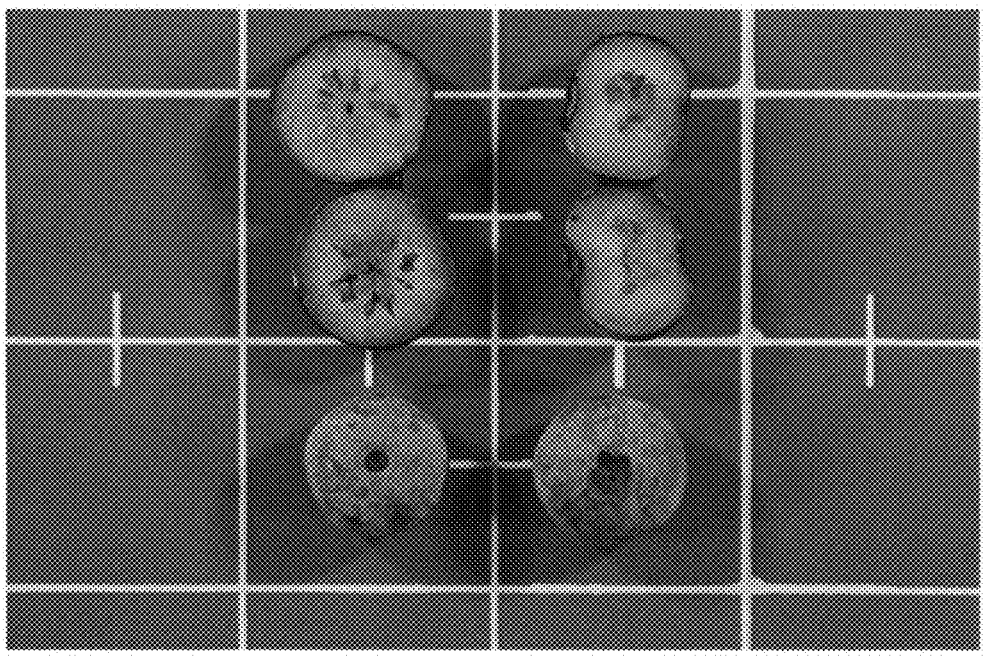
FIG. 3 is a photograph taken of mature fruits of 'Norman' showing whole and cut berries.
Figure 4:
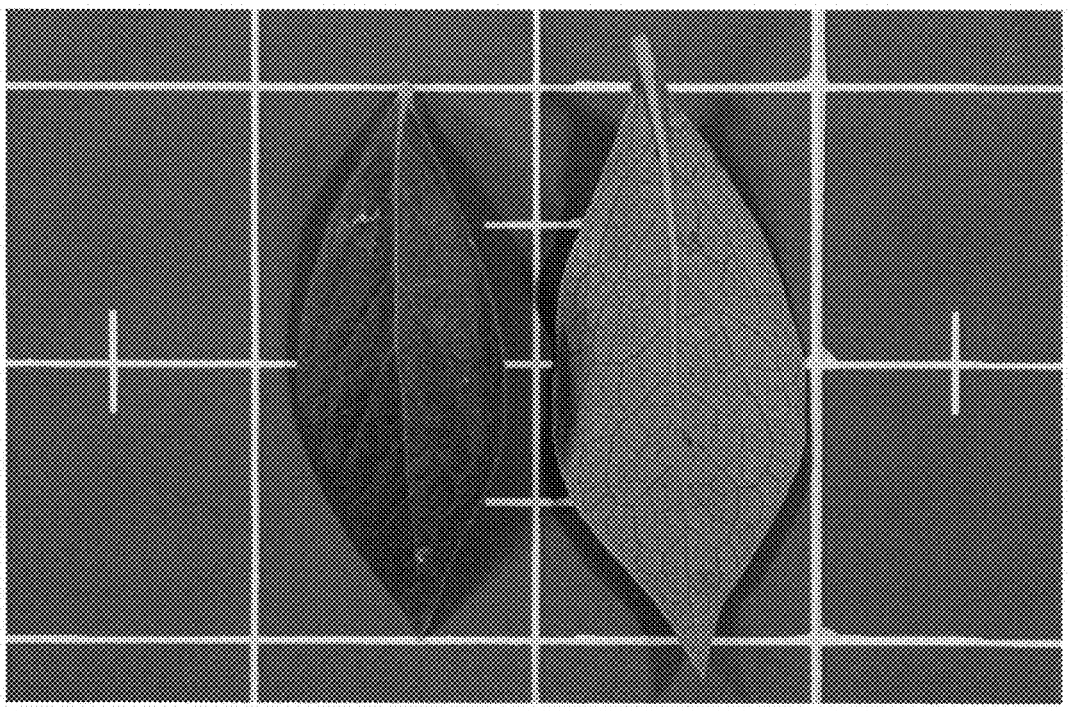
FIG. 4 is a photograph showing the adaxial (upper) and abaxial (lower) sides of leaves of 'Norman'.

Plants and fruit of this new cultivar differ phenotypically from its parents. The new cultivar is more productive and has healthier plants, has lighter fruit color, is firmer and has improved flavor compared to female parent USDA Selection G-566. It has fruit that is lighter in color and firmer than male parent 'Legacy'. The new cultivar and its progenitors phenotypically exhibit characters predominately of the highbush blueberry species, *Vaccinium corymbosum* (highbush blueberry). The new cultivar of blueberry is an interspecific hybrid, derived from crossing three *Vaccinium* species: *V. angustifolium, V. corymbosum,* and *V. darrowi*. The new cultivar phenotypically exhibits plant and fruit characters predominately of the highbush blueberry, *Vaccinium corymbosum*, but may possess genes for wider environmental and soil adaptability characteristic of it's *V. angustifolium* and *V. darrowi* progenitors.

Plants of the new cultivar are moderately vigorous, with vigor ratings/observations similar to those for 'Bluecrop' and 'Ozarkblue'. The chilling requirement of the cultivar has not been fully determined, but is estimated to be approximately 500 hours (hours below 7° C./45° F.). It is lower chilling than the comparison cultivars 'Ozarkblue' and 'Bluecrop' as indicated by its earlier budbreak in late winter; these two cultivars have a chilling requirement of 800 hours or more. 'Norman' did not perform well in an area of chill of approximately 300 hours (Oxnard, Calif.). No diseases were observed on the plants although stem blight [*Botryosphaeria dothidea* (Mouq. ex Fr.) Ces & de Not] has been observed at the evaluation site near Clarksville, Ark. No fruit diseases were observed, despite the plants having no fungicide applications during evaluation in Arkansas.

Flower bud swell of the new cultivar averaged 17 February near Clarksville, Ark., earlier compared to 10 to 14 March for 'Bluecrop' and 'Ozarkblue'. Bloom date (50% bloom) averaged 31 March, earlier than 'Bluecrop' of 10 April and 'Ozarkblue' of 13 April. The earlier bud swell resulted in late winter freeze damage to developing buds in some years in Arkansas.

Average 10% ripe fruit of the new cultivar is 3 June, near that of 'Bluecrop' and 5 days before 'Ozarkblue'. Fruit yields of the new cultivar are up to 3.8 kg/plant (8.4 lb), compared to 2.9 kg/plant (6.4 lb) for 'Bluecrop', and 7.5 kg/plant (16.5 lb) for 'Ozarkblue' in West-Central Arkansas.

The fruit is oblate. Berries are light blue in color with whitish waxy bloom on fruit surface and have outstanding appearance. Berries are medium-large to large (1.5-2.2 g). The stem scar of the fruit is smaller than 'Bluecrop' and similar to 'Ozarkblue'. Fruit firmness was rated higher than 'Bluecrop' or 'Ozarkblue', a major attribute of 'Norman'. Fruit firmness measurements were very high before and after 14 days of storage. The storage (shipping) potential of fresh fruit of the new cultivar is very high due to this firmness.

The fresh fruit is very good in flavor. The fresh fruit was more aromatic and sweeter than 'Bluecrop'. Its flavor is less acidic than 'Ozarkblue'. The soluble solids concentration averages 9.7 to 10.7% on ripe fruit. Seeds average 65/berry and are small and soft.

The following is a detailed description of the botanical and pomological characteristics of the subject blueberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were 11 years old and grown on a fine sandy loam soil with trickle irrigation near Clarksville, Ark. The plants were fertilized near budbreak (late March on average) with complete or nitrogen fertilizer, and had an additional nitrogen fertilizer application in early July. Weeds were controlled with pre- and post-emergence herbicides supplemented with mechanical weed control activities. The descriptions reported herein are from specimens grown near Clarksville, Ark. unless otherwise noted.

Plant:

*Size*.—Medium; similar to other highbush blueberry varieties. Height: 120 cm. Width: 110 cm.

*Growth habit*.—Upright; moderate vigor; moderate cane production from crown.

*Productivity*.—3.8 kg/plant (8.4 lb).

*Cold hardiness*.—Hardy to −18° C. (0° F.) or possibly lower. Early bud swell has resulted in frost damage to developing buds and subsequent early flowers in some years in Arkansas.

*Chilling requirement*.—Approximately 500 hours (hours below 7° C./45° F.).

*Canes*.—Cane mature/5-7 years of age (dormant): diameter at cane base: 2.01 cm; diameter at cane midpoint 1.25 cm; diameter at cane terminus: 0.48 cm. Cane one-year-old (dormant): diameter at cane base: 0.73 cm; diameter at midpoint: 0.57 cm; diameter at terminus: 0.37 cm. Mature cane color (dormant): base: Greyed-green 197-A; midpoint: Greyed-green 197-A; terminus: Grayed-orange group 166-B. One-year-old cane color (dormant): base: Greyed-orange 174-A; midpoint: Greyed-orange 174-A; terminus: Greyed-brown 199-A to Greyed-orange 165-B.

*Branch/stem*.—Current seasons growth at the end of the growing season: Leaf internode length: 1.42 cm. Average stem length: 20.0 cm. Stem pubescence: none. Average number of flower buds: 5.3.

*Disease resistance*.—No diseases were observed on the plants despite the plants having no fungicide applications during evaluation in Arkansas.

Foliage:

*Leaves*.—Size: Medium. Mature leaf diameter: 2.53 cm. Length: 6.66 cm. Mature leaf color: base abaxial: Yellow-green group 147-C; base adaxial: Green group 137-A; midpoint abaxial: Yellow-green group 147-C; midpoint adaxial: Green group 132-A; terminal abaxial: Yellow-green group 147-C; terminal adaxial-Green group 137-A. Mature leaf shape: lanceolate; tip: acute; base: cuneate. Evergreen/deciduous: deciduous. Mature leaf pubescence: abaxial: none; adaxial: none. Leaf serration: no serration visible; entire.

*Petiole*.—Length: 0.37 cm. Color: Yellow green group 144-B.

Flowers:

*Date of flower bud swell* (*stage* 2).—17 February.

*Date of bloom*.—10%; full: 31 March.

*Inflorescence size*.—Medium.

*Corolla color*.—White group 155-D.

*Corolla shape*.—Cylindrical.

*Reproductive organs*.—Stamens: erect, numerous; Pistils: one per flower; Calyx: 5 lobed.

*Pollen*.—Normal and abundant.

*Average number of flowers per cluster*.—5.6.

*Average flower length*.—9.40 mm.

*Average flower width*.—5.76 mm.

*Number of petals per flower*.—5, fused to form a corolla tube.

*Average pedicel length*.—5.08 mm.

*Pedicel color*.—Yellow-green group 144-A.

*Number of sepals*.—5, fused.

*Sepal color*.—Green group 143-C.

*Number of stamens*.—10.

*Anther color*.—Grayed orange group 165-B.

*Stigma color*.—Yellow green group 153-C.

*Average stigma length*.—0.63 mm.

Fruit:

*Size*.—Medium-large. Weight: 1.5-2.2 g. Diameter: Primary fruit at equator: 1.41 cm. Thickness of primary fruit (scar to mid-calyx): 1.09 cm. Secondary fruit at equator: 1.62 cm. Thickness of secondary fruit (scar to mid-calyx): 1.21 cm. Tertiary fruit at equator: 1.59 cm. Thickness of fruit (scar to mid-calyx): 1.19 cm.

*Maturity*.—Average 10% ripe date: June 3. Average period of ripening: June 3 to June 20.

*Shape*.—Oblate, uniform.

*Firmness*.—Berries are very firm, with firmness of 2.2 N at harvest compared to 1.3 N for Bluecrop, Ozarkblue and Summit.

*Color*.—Bloom undisturbed (with whitish wax bloom on surface): Violet-blue 95-D. Bloom removed: Black group 202-A. Unripe fruit flesh: yellow-green group 145C and unripe fruit skin yellow-green group 145A. Ripe fruit color: yellow green group 145C.

*Pedicel scar size*.—Small, 2.12 mm.

*Soluble solids*.—10.7% brix.

*pH*.—3.32.

*Total acidity*.—0.4 g/100 mL expressed as citric acid.

*Berries per cluster*.—=5.6.

*Density of fruit cluster*.—Medium.

*Fruiting type*.—Fruits on one year old shoots only.

*Storage potential*.—Berries have good storage potential as they did not decline in firmness in 14 days of storage at 5° C.

*Calyx*.—Width: =4.6 mm. Depth: =1.3 mm.

Seeds:

*Weight* (*wet*).—0.40 mg.

*Weight* (*dry*).—0.24 mg.

*Length*.—1.65 mm.

*Width*.—0.81 mm.

*Size*.—Small, soft.

*Number per berry*.—65.

*Color* (*wet*).—Grayed orange group 166-B.

*Color* (*dry*).—Grayed orange group 166-B.

*Self-compatibility*.—Not tested.

Uses: Fresh, ideal for shipping and local sales markets.

The cultivar: The most distinctive features of the cultivar are high fruit quality including excellent picking scar, color, firmness and flavor along with excellent plant health and vigor.

We claim:

1. A new and distinct cultivar of blueberry plant named 'Norman', substantially as illustrated and described herein.

* * * * *